(12) United States Patent
Kohler

(10) Patent No.: US 10,952,530 B2
(45) Date of Patent: Mar. 23, 2021

(54) DOUBLE-ENDED ILLUMINATED DENTAL TOOL WITH REPLACEABLE ATTACHMENTS

(71) Applicant: ONVI, Inc., Wilmette, IL (US)

(72) Inventor: Craig Kohler, Glenview, IL (US)

(73) Assignee: ONVI, Inc., Wilmette, IL (US)

( * ) Notice: Subject to any disclaimer, the term of this patent is extended or adjusted under 35 U.S.C. 154(b) by 62 days.

(21) Appl. No.: 16/477,638

(22) PCT Filed: Mar. 27, 2019

(86) PCT No.: PCT/US2019/024368
§ 371 (c)(1),
(2) Date: Jul. 12, 2019

(87) PCT Pub. No.: WO2019/191290
PCT Pub. Date: Oct. 3, 2019

(65) Prior Publication Data
US 2020/0375346 A1    Dec. 3, 2020

Related U.S. Application Data

(60) Provisional application No. 62/648,901, filed on Mar. 27, 2018.

(51) Int. Cl.
*A46B 9/04* (2006.01)
*A46B 15/00* (2006.01)
(Continued)

(52) U.S. Cl.
CPC ........ *A46B 15/0036* (2013.01); *A46B 5/0095* (2013.01); *A46B 9/04* (2013.01);
(Continued)

(58) Field of Classification Search
CPC ..... A46B 5/0095; A46B 9/04; A46B 15/0036; A46B 15/0069; A46B 15/0077;
(Continued)

(56) References Cited

U.S. PATENT DOCUMENTS 5,230,118 A    7/1993  Chamma
5,743,731 A *  4/1998  Lares ................ A61B 1/00087
                                                433/29
(Continued)

FOREIGN PATENT DOCUMENTS

EP    2 891 467 A1 *   7/2015

OTHER PUBLICATIONS

ISA/US, International Search Report and Written Opinion issued in PCT/US2019/024368, dated Jun. 11, 2019, 9 pgs.

*Primary Examiner* — Randall E Chin
(74) *Attorney, Agent, or Firm* — Greenberg Traurig, LLP

(57) ABSTRACT

An example embodiment of a dental tool includes a main body portion having a first longitudinal end and a second longitudinal end, wherein the first end and the second end define respective reduced diameter portions, two or more tool attachments, each tool attachment comprising a working portion and a base portion, the base portion configured to be removably coupled to either of the reduced-diameter portions of the main body portion so as to secure the tool attachment to the main body portion, and a light source, disposed within the main body portion, arranged so as to illuminate the working portion of one of the tool attachments when the one of the tool attachments is coupled to the first end of the main body portion and the light source is electrically coupled to a power source.

14 Claims, 10 Drawing Sheets

(51) Int. Cl.
  *A61B 1/06* (2006.01)
  *A61C 3/00* (2006.01)
  *A61C 17/18* (2006.01)
  *A61B 1/247* (2006.01)
  *A46B 5/00* (2006.01)

(52) U.S. Cl.
  CPC ...... *A46B 15/0069* (2013.01); *A46B 15/0077* (2013.01); *A46B 15/0081* (2013.01); *A61B 1/06* (2013.01); *A61B 1/247* (2013.01); *A61C 3/00* (2013.01); *A61C 17/18* (2019.05); *A46B 2200/1066* (2013.01)

(58) Field of Classification Search
  CPC ........ A46B 15/0081; A46B 2200/1066; A61B 1/247; A61B 1/06; A61B 1/0623; A61B 1/063; A61C 3/00; A61C 17/18
  See application file for complete search history.

(56) References Cited

U.S. PATENT DOCUMENTS

| | | |
|---|---|---|
| 2006/0029906 A1 | 2/2006 | Hill |
| 2007/0121786 A1 | 5/2007 | Okawa et al. |
| 2008/0044788 A1 | 2/2008 | Jansheski |
| 2014/0023984 A1* | 1/2014 | Weatherly ............. A61B 1/247 433/31 |
| 2016/0157597 A1 | 6/2016 | Oralucent |
| 2018/0235727 A1 | 8/2018 | Rubino et al. |

* cited by examiner

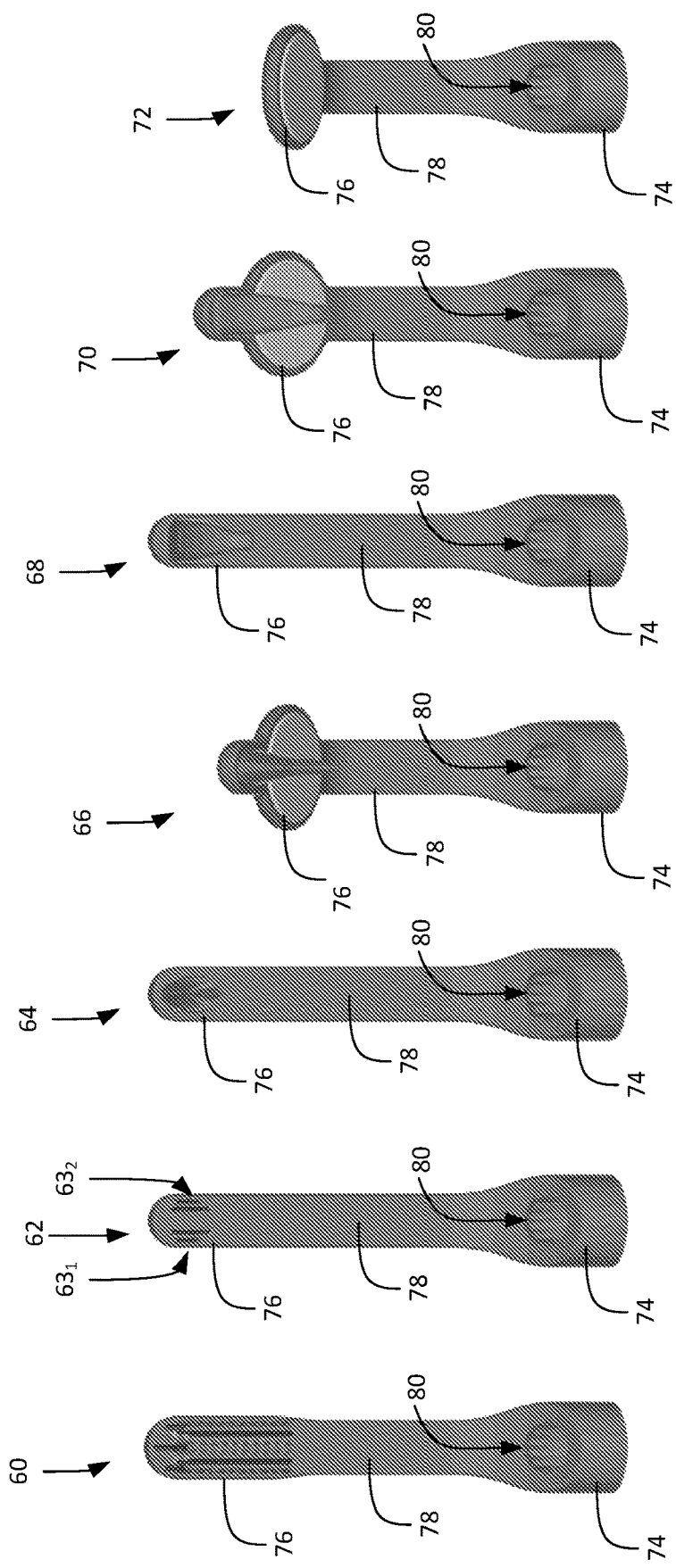

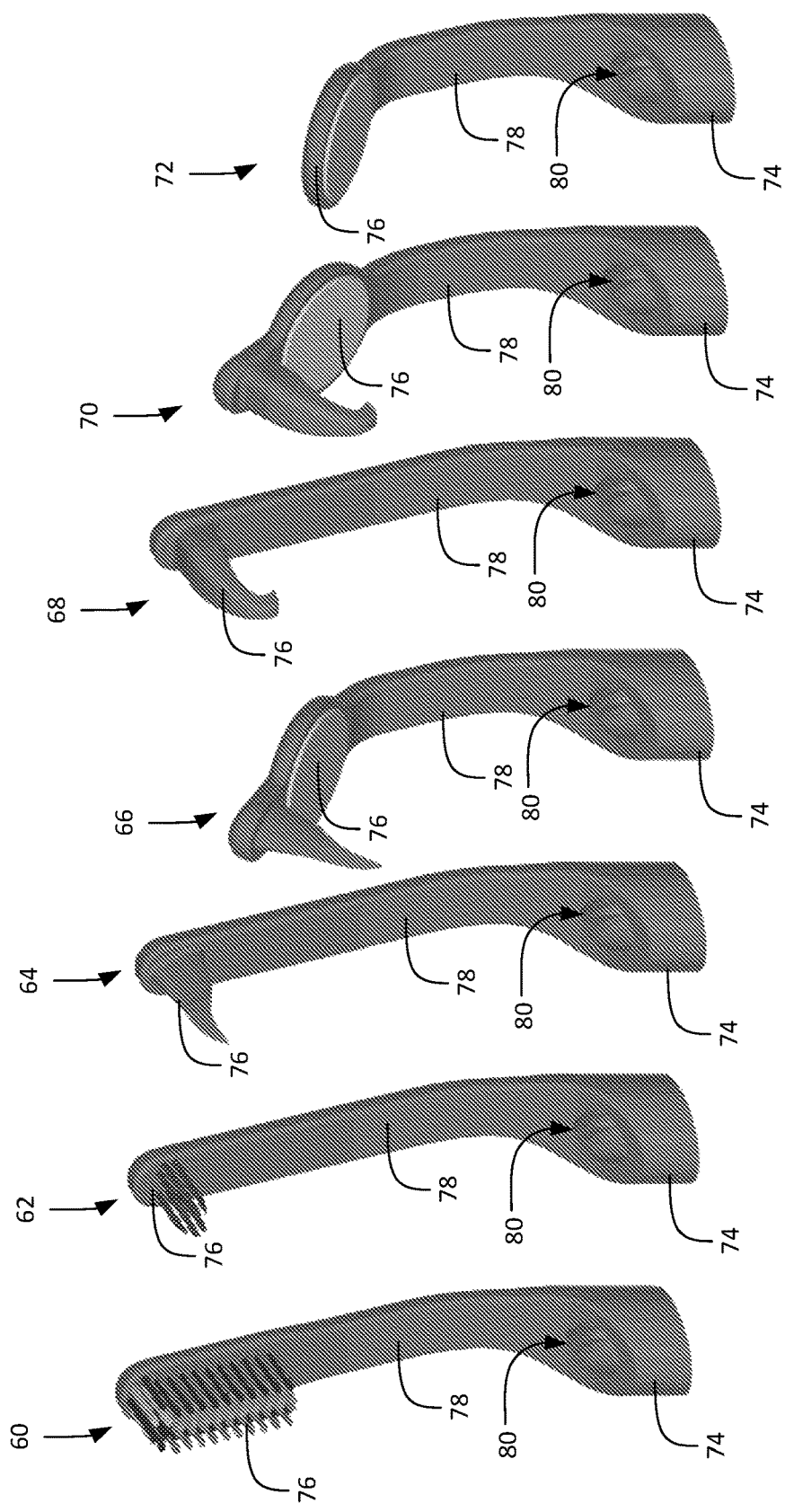

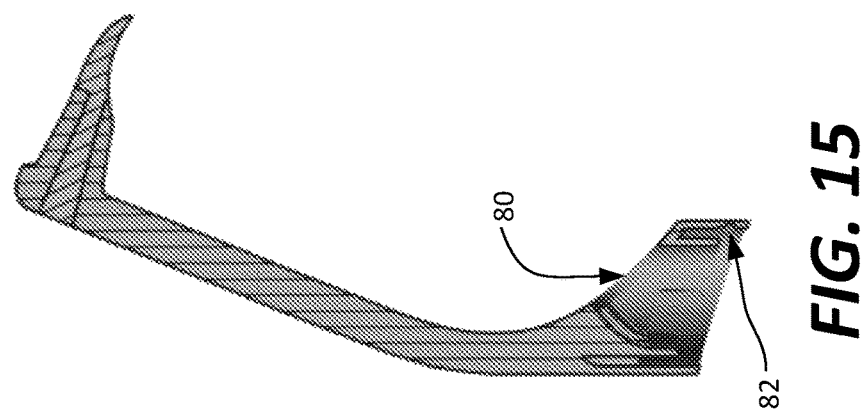
FIG. 15
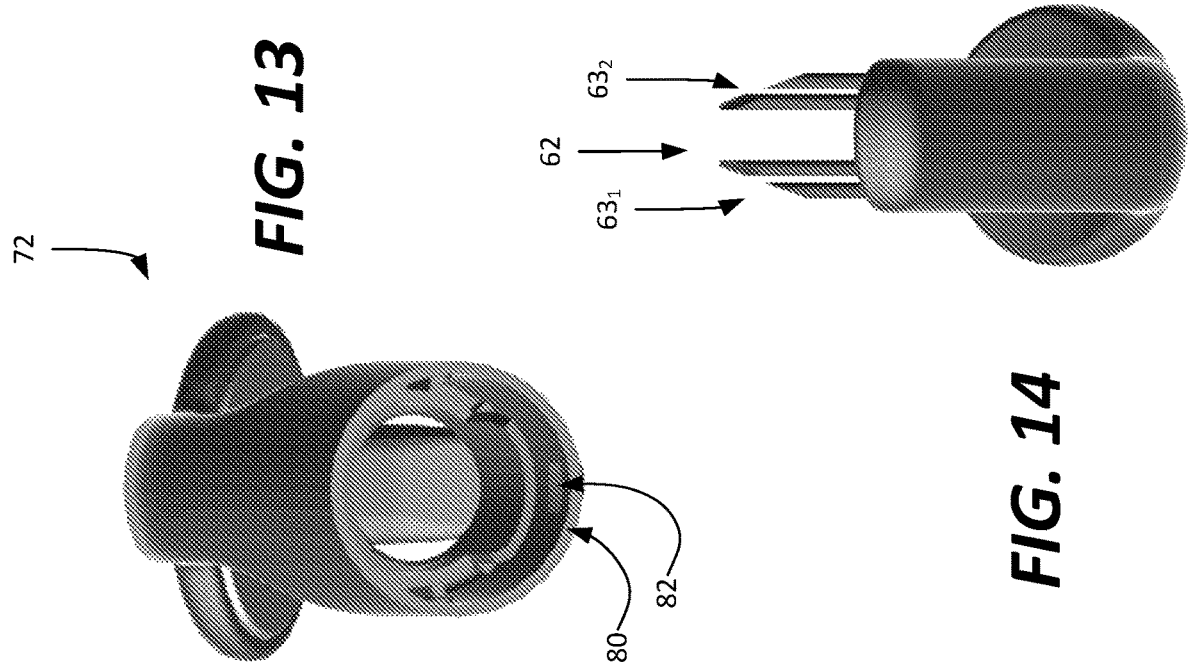
FIG. 13
FIG. 14

DOUBLE-ENDED ILLUMINATED DENTAL TOOL WITH REPLACEABLE ATTACHMENTS

CROSS-REFERENCE TO RELATED APPLICATION

This application claims the benefit of priority to U.S. application No. 62/648,901, filed Mar. 27, 2018, which application is hereby incorporated by reference in its entirety.

BACKGROUND

The present disclosure relates to devices for oral care, including manual care in conjunction with orthodontia. The devices of the present disclosure may also find use for a user without orthodontia.

Orthodontic treatments, such as braces, retainers, and the like, may be difficult for a user (e.g., wearer of the treatment) to clean and maintain, and may make it difficult for a user to clean his or her teeth. Even in the absence of orthodontia, existing tools for spot cleaning a user's teeth (e.g., tools other than toothbrushes) may not be sufficiently reusable or of sufficient quality to fulfill a user's needs.

SUMMARY

An example embodiment of a dental tool includes a main body portion having a first longitudinal end and a second longitudinal end, wherein the first end and the second end define respective reduced diameter portions, two or more tool attachments, each tool attachment comprising a working portion and a base portion, the base portion configured to be removably coupled to either of the reduced-diameter portions of the main body portion so as to secure the tool attachment to the main body portion, and a light source, disposed within the main body portion, arranged so as to illuminate the working portion of one of the tool attachments when the one of the tool attachments is coupled to the first end of the main body portion and the light source is electrically coupled to a power source.

In some embodiments, the respective base portion of each of the two or more tool attachments defines an aperture, and one of the reduced-diameter portions of the main body portion extends through the aperture of any one of the tool attachments when the one of the tool attachments is coupled to the main body portion.

In some embodiments, the main body portion defines a longitudinal axis, and the longitudinal axis extends through the aperture of any one of the tool attachments when the one of the tool attachments is coupled to the main body portion.

In some embodiments, the light source projects light from the reduced-diameter portion of the first end.

In some embodiments, the dental tool includes a light-transmissive cover disposed at the reduced-diameter portion of the first end, wherein the light source and the light-transmissive cover are arranged such that the light source emits light through the light-transmissive cover, wherein the light-transmissive cover is flush with a surface of the base portion of any one of the tool attachments when the one of the tool attachments is coupled to the main body portion.

In some embodiments, an outer diameter of the base portion of any one of the tool attachments is substantially the same as an outer diameter of the main body portion that is immediately longitudinally adjacent to the base portion when the one of the tool attachments is coupled to the main body portion.

In some embodiments, the dental tool includes a battery disposed within the main body portion, and a switch disposed on or in the main body portion, the switch configured to selectively couple the light source to the battery responsive to user actuation of the switch.

In some embodiments, the main body portion is substantially cylindrical along its entire longitudinal length.

In some embodiments, the light source is a first light source, and the dental tool further includes a second light source, disposed within the main body portion, arranged so as to illuminate the working portion of one of the tool attachments when the one of the tool attachments is coupled to the second end of the main body portion and the second light source is electrically coupled to a power source.

In some embodiments, the first light source projects light at a first angle relative to a longitudinal axis of the main body portion, the second light source projects light at a second angle relative to the longitudinal axis, and the first angle has substantially the same absolute value as the second angle.

In some embodiments, the first light source is arranged to project light in a first direction, the second light source is arranged to project light in a second direction, and the first direction is radially opposite the second direction.

In some embodiments, the dental tool further comprises a battery disposed within the main body portion, a first switch disposed on or in the main body portion, the switch configured to selectively couple the first light source to the battery responsive to user actuation of the first switch, and a second switch disposed on or in the main body portion, the second switch configured to selectively couple the second light source to the battery responsive to user actuation of the second switch, wherein the second switch is radially opposite the first switch.

In some embodiments, the two or more tool attachments comprise two or more of a bristle brush tool attachment, an orthodontic brush tool attachment, a scaler tool attachment, a scaler with mirror tool attachment, a scraper tool attachment, a scraper with mirror tool attachment, a mirror tool attachment, or an interproximal brush tool attachment.

In some embodiments, the two or more tool attachments comprise an orthodontic brush tool attachment comprising two sets of bristles that are laterally separated from each other, wherein bristles within each set increase in length from an outer later edge of the orthodontic brush tool attachment to an inner lateral portion of the orthodontic brush tool attachment.

In some embodiments, the two or more tool attachments comprise a scaler tool attachment, the scaler tool attachment comprising a removable working tip that is insertable into a receiving formation of a neck of the scaler tool attachment, the removable working tip comprising a lateral protrusion, wherein the receiving formation defines two or more recesses configured to receive the lateral protrusion of the working tip, whereby the removable working tip may be coupled in two or more positions relative to the neck.

BRIEF DESCRIPTION OF THE DRAWINGS

FIGS. 6A and 6B are front and perspective views, respectively, of an example embodiment of a bristle brush tool attachment that may find use with a double-ended dental tool according to the present disclosure.

FIGS. 7A and 7B are front and perspective views, respectively, of an example embodiment of an orthodontic brush tool attachment that may find use with a double-ended dental tool according to the present disclosure.

FIGS. 8A and 8B are front and perspective views, respectively, of an example embodiment of a scaler tool attachment that may find use with a double-ended dental tool according to the present disclosure.

FIGS. 9A and 9B are front and perspective views, respectively, of an example embodiment of a scaler with mirror tool attachment that may find use with a double-ended dental tool according to the present disclosure.

FIGS. 10A and 10B are front and perspective views, respectively, of an example embodiment of a scraper tool attachment that may find use with a double-ended dental tool according to the present disclosure.

FIGS. 11A and 11B are front and perspective views, respectively, of an example embodiment of a scraper with mirror tool attachment that may find use with a double-ended dental tool according to the present disclosure.

FIGS. 12A and 12B are front and perspective views, respectively, of an example embodiment of a mirror tool attachment that may find use with a double-ended dental tool according to the present disclosure.

FIG. 13 is a lower perspective view of the example mirror tool attachment of FIGS. 12A and 12B.

FIG. 14 is a top view of the example orthodontic brush tool attachment of FIGS. 7A and 7B.

FIG. 15 is a cross-sectional view of the example scaler tool attachment of FIGS. 8A and 8B.

DETAILED DESCRIPTION

The instant disclosure provides a double-ended dental tool for oral care, including for cleaning a user's teeth and orthodontic treatments. The tool may include opposed ends, with one or both of the ends having removable and replaceable tool attachments, including one or more scrapers, mirrors, scalers, brushes, and the like. The tool attachments may be interchangeable, such that a user may arrange the attachment configuration that the user prefers (e.g., a scraper and a scaler, or a scaler and a mirror, or a mirror and a brush, etc.). The tool attachments may also be durable, such that each attachment may be used by a user numerous times before requiring replacement. In addition, the tool may include a light source at one or both ends for illuminating attached tools.

Figure 1:
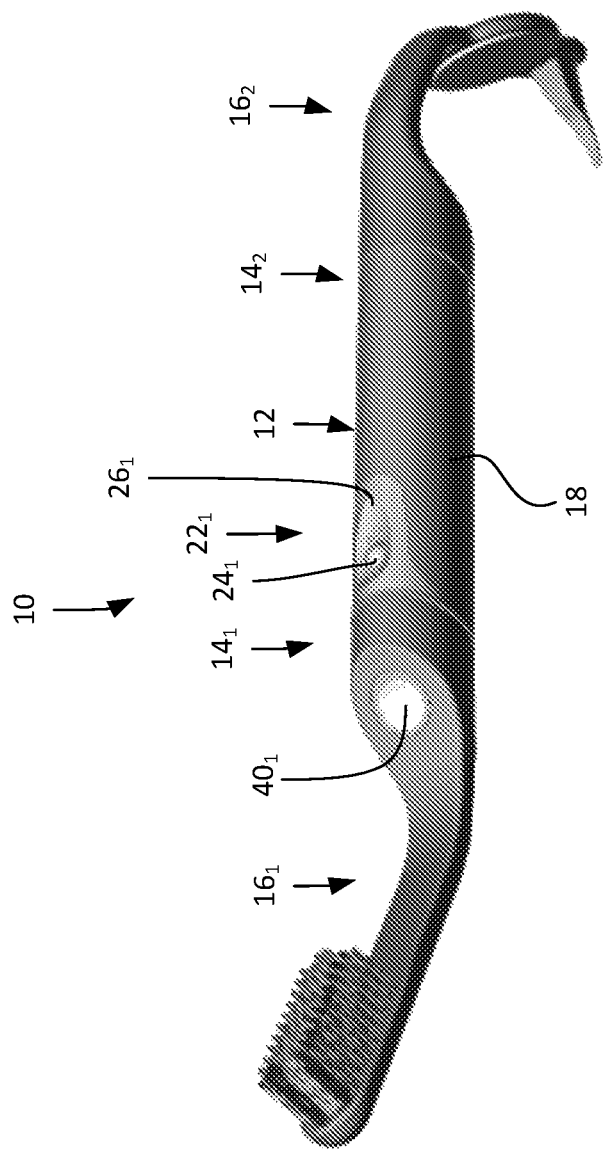
FIG. 1 is a perspective view of an example embodiment of a double-ended dental tool with attached tools.
Figure 2:
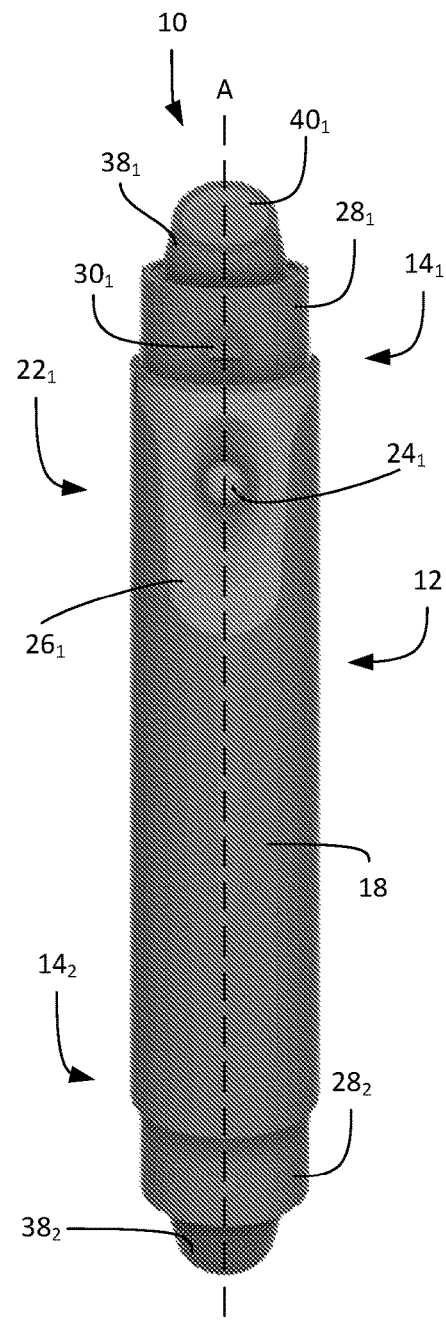
FIGS. 2 and 3 are front and side views, respectively, of the example double-ended dental tool of FIG. 1, without attached tools.
Figure 3:
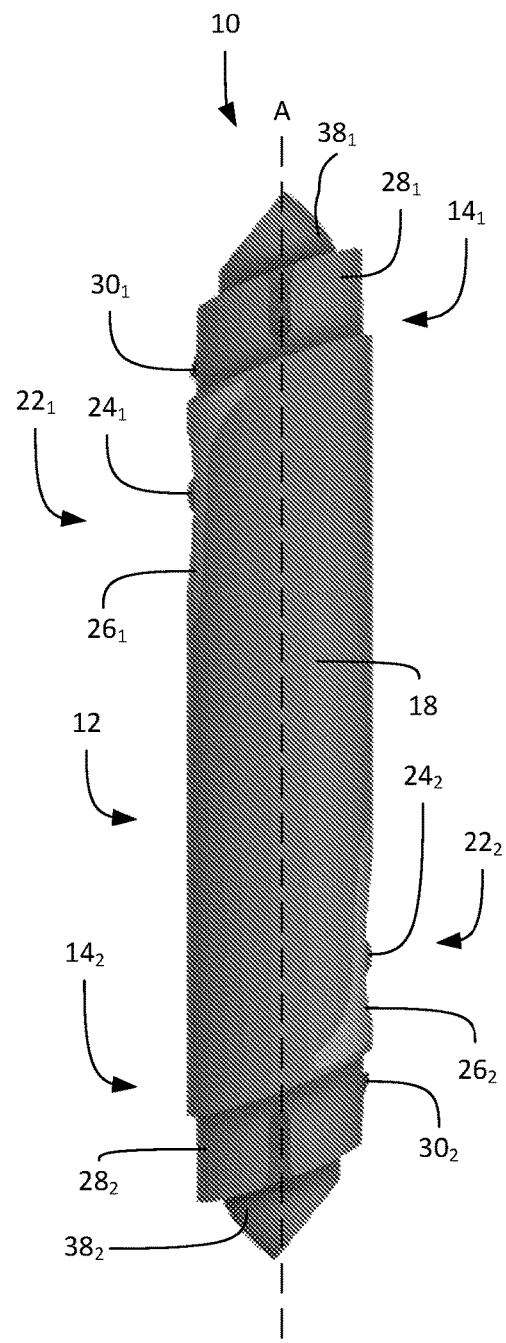
Figure 4:
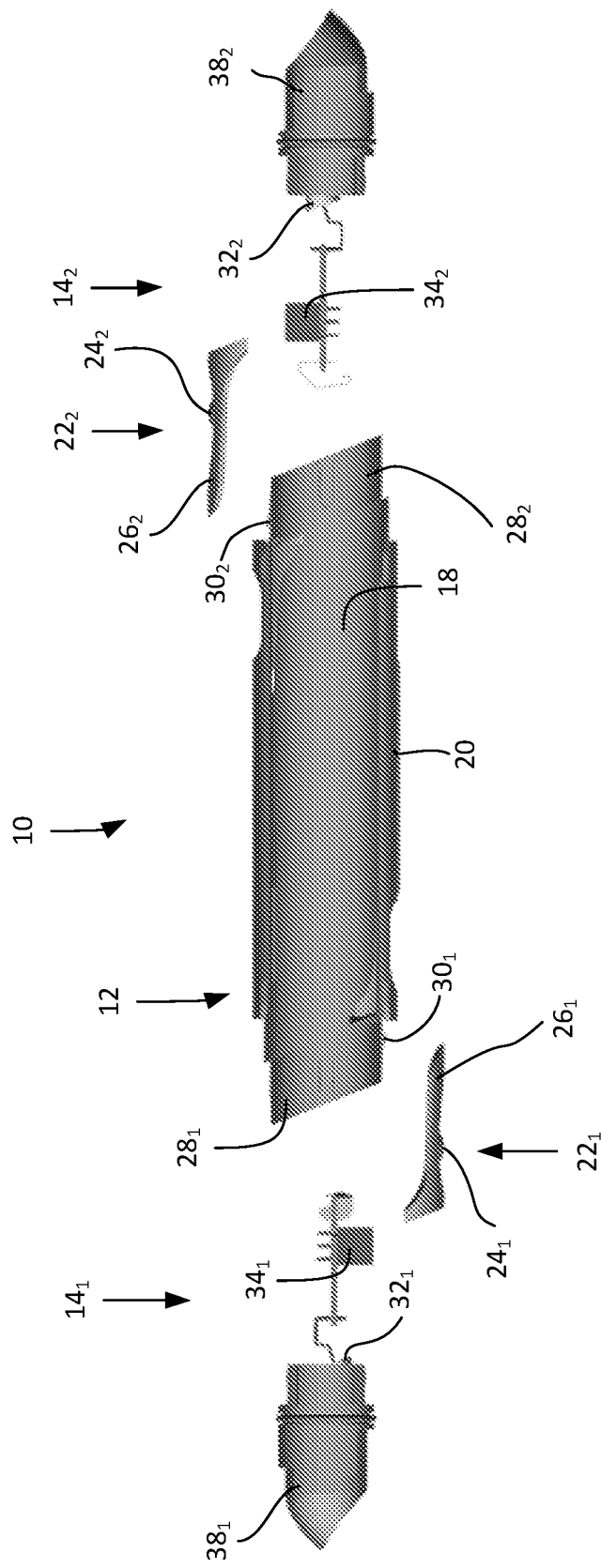
FIG. 4 is a partially-exploded view of the example double-ended dental tool of FIG. 1, without attached tools.
Figure 5:
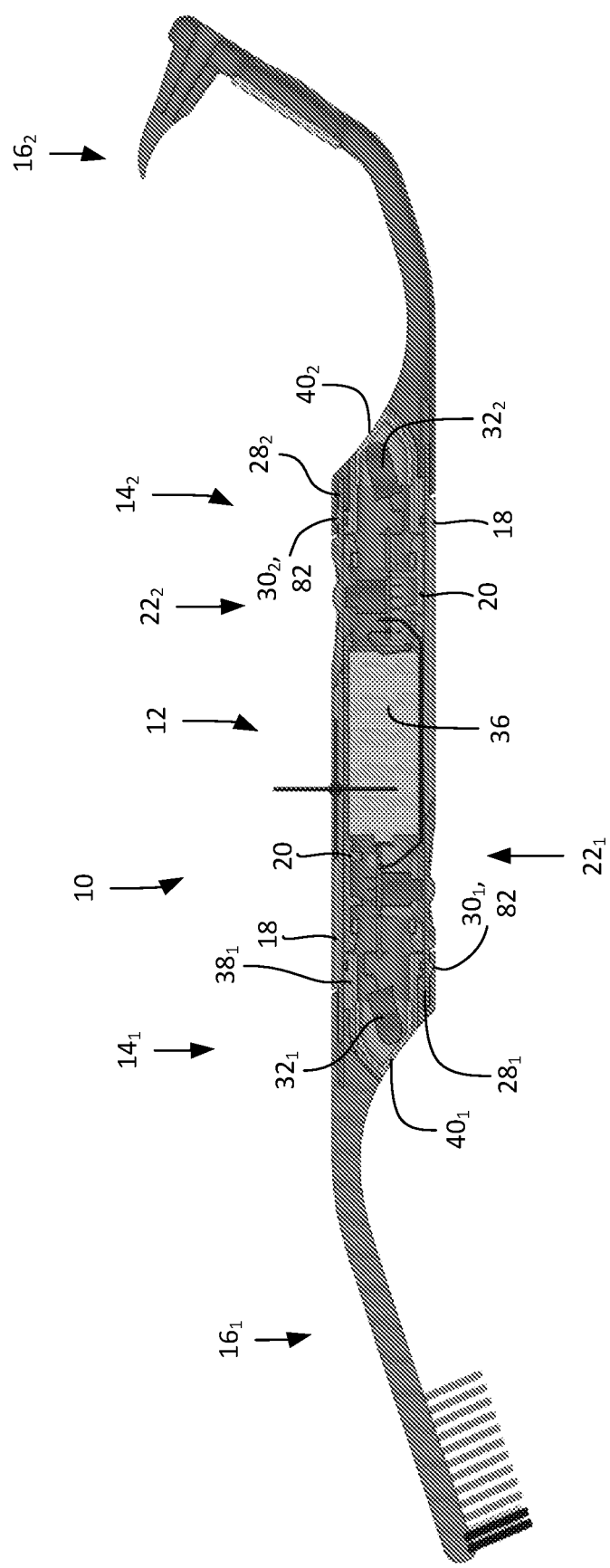
FIG. 5 is a cross-sectional view of the example double-ended dental tool of FIG. 1, with attached tools.

FIGS. 1-5 are various views of an example embodiment of a double-ended dental tool 10. FIGS. 1 and 5 illustrate the double-ended tool 10 with attachments. In contrast, FIGS. 2, 3, and 4 illustrate the double-ended tool 10 without attachments. The double-ended tool 10 may include a main body portion 12, a first longitudinal end $14_1$, and a second longitudinal end $14_2$. A first attachment $16_1$ may be removably coupled to the main body 12 at the first end $14_1$, and a second attachment $16_2$ may be removably coupled to the second end $14_2$. When attached, the first tool $16_1$, or a portion thereof, may extend at an angle from the main body portion 12, and the second tool $16_2$ may extend at the opposite angle.

The main body portion 12 may include an outer cylindrical portion 18 and an inner cylindrical portion 20 (shown in FIGS. 4 and 5) that is disposed radially inward of the outer cylindrical portion 18. The outer cylindrical portion may define a central longitudinal axis A (illustrated in FIGS. 2 and 3). References in this disclosure to longitudinal or radial relationships are with reference to directions defined by the axis A. The main body portion 12 may have an outer profile that is substantially cylindrical along the entire longitudinal length of the main body portion 12. The main body portion 12 may further include switch portions $22_1$, $22_2$ on radially opposite sides of the main body portion 12 and at opposite longitudinal ends $14_1$, $14_2$ of the main body portion 12. The switch portions 22 may include respective buttons $24_1$, $24_2$, and switch surfaces $26_1$, $26_2$. Each button 24 may operate a respective light source (as will be described below).

Although the switch portions 22 are illustrated and described herein as including buttons 24, other switch types may find use in the tool 10. For example, slider switches, twist-style switches, or any other appropriate type of switches may be included in the tool 10 for actuation by the user to operate light sources of the tool 10.

Each end $14_1$, $14_2$ of the main body portion 12 may include a respective reduced-diameter portion $28_1$, $28_2$. In an embodiment, the reduced-diameter portion is a portion of the outer cylindrical portion 18, as illustrated in FIGS. 1-5.

The attachments 16 may couple with the reduced-diameter portions 28 so as to couple the attachments with the main body portion 12. In an embodiment, each reduced diameter portion $28_1$, $28_2$ may include a mating formation $30_1$, $30_2$ which may mate with a counterpart formation on an attachment 16 (as will be described below). In an embodiment, each mating formation 30 may be a protrusion on the reduced-diameter portion 28.

The double-ended tool 10 may include one or more light sources $32_1$, $32_2$ (shown in FIGS. 4 and 5) for selectively illuminating the attachments $16_1$, $16_2$. The light sources $32_1$, $32_2$ may be disposed at the first end $14_1$ and the second end $14_2$, respectively. The light sources 32 may be disposed within the main body portion 12. The light sources 32 may be or may include light-emitting diodes (LEDs), in an embodiment. In other embodiments, the light sources 32 may be or may include alternate types of light sources, such as halogen, fluorescent, or another light source type. In some embodiments, one or both of the light sources may emit light in the visible spectrum when coupled with a power source. In an embodiment, one or both of the light sources 32 may emit ultraviolet light when coupled with a power source. The light sources 32 may be arranged so as to illuminate the working portion of a tool attachment when the tool attachment is coupled to the main body portion 12 and the light source is electrically coupled to a power source.

The light sources $32_1$, $32_2$ may be electrically coupled with respective electrical switches $34_1$, $34_2$ which may be in physical contact with the buttons $24_1$, $24_2$ and which may further be electrically coupled with a power source such that, when a user actuates a button 24, the electrical switch 34 electrically couples a respective light source 32 to, or electrically decouples a respective light source from, the power source (e.g., via one or more printed circuit boards (PCBs), electrical contacts, and/or other appropriate electrical coupling devices). The power source may be a battery 36 (shown in FIG. 5), in some embodiments. In the example of FIGS. 4 and 5, the first button $24_1$ actuates the first electrical switch $34_1$. When actuated, the first electrical switch $34_1$ couples the first light source $32_1$ to, or decouples the first light source $32_1$ from, the battery 36. Similarly, the second button $24_2$ actuates the second electrical switch $34_2$. When actuated, the second electrical switch $34_2$ couples the second light source $32_2$ to, or decouples the second light source $32_2$ from, the battery 36.

The double-ended tool 10 may further include a respective light housing $38_1$, $38_2$ associated with each light source $32_1$, $32_2$. Each light housing 38 may be disposed radially about its respective light source 32. Each light housing 38 may be disposed within the main body portion 12, radially-inward from the outer body portion 18. The light housing 38 may be waterproof when properly disposed within the main body portion 12. Accordingly, each light housing 38 may be coupled with a gasket or other sealing device around the periphery of the light housing 38 so as to prevent ingress of fluid into the main body portion 12. The main body portion 12 may be fluid-tight, in embodiments, to prevent exposure of electrical components within the main body portion 12 to liquid. Fluid tight construction may be provided by, for example, tightness of fit between and among cylindrical portions 18, 20 of the main body portion, battery housings, and light covers (described below), as well as by one or more gaskets or other sealing devices as described herein.

Each light housing $38_1$, $38_2$ may include a respective light-transmissive cover $40_1$, $40_2$ that permits light from a respective light source 32, such that the light source 32 emits light through the light-transmissive cover 40 to illuminate an attachment 16. A light-transmissive cover may comprise, for example, acrylic material, in embodiments. Each light-transmissive cover 40 may be disposed at a longitudinal end of the main body portion 12, such that light is emitted from a longitudinal end of the main body portion 12 when a light source 32 is coupled with the power source. Further, each light-transmissive cover 40 may be provided within a reduced-diameter portion 28 of the main body portion 12, such that a light source 32 projects light from the reduced-diameter portions of the main body portion 12. Each light cover $40_1$, $40_2$ and light source $32_1$, $32_2$ may be oriented so that an attachment is illuminated by the light source 32. For example, the light cover 40 may be angled at between 30 and 60 degrees relative to the longitudinal axis A, in some embodiments. The light cover 40 may be angled at between 35 and 55 degrees relative to the longitudinal axis A, in some embodiments. The light cover 40 may be angled at between 40 and 50 degrees relative to the longitudinal axis A, in some embodiments. The light cover 40 may be angled at approximately 45 degrees relative to the longitudinal axis A, in some embodiments. The light covers $40_1$, $40_2$ may be angled in opposite directions from the axis A, with the same absolute value of the angle, as illustrated in FIGS. 1-5, in some embodiments. In other words, the light covers 40 may be arranged on radially-opposite sides of the main body portion 12, in embodiments, as illustrated in FIGS. 1-5. In an embodiment, a light source 32 may project light at an angle relative to the longitudinal axis A that is the same as the angle between the axis A and the light cover 40 associated with that light source 32.

Each light housing 38 may include, at its longitudinal end, a reduced-diameter portion that is radially separated from a reduced-diameter portion of the outer cylindrical portion 18 so as to define an annular space therebetween. As will be described below, an attachment 16 may interact with the annular space between the reduced-diameter portion of the light housing 38 and the reduced-diameter portion 28 of the outer cylindrical portion 18 so as to secure the attachment 16 to the main body portion 12.

The outer cylindrical portion 18 may comprise a thermoplastic polymer, such as acrylonitrile butadiene styrene, for example only, in some embodiments. In other embodiments, the outer cylindrical portion 18 may comprise metal or another rigid material.

The switch portions 22 may comprise a thermoplastic elastomer, thermoplastic polyurethane, and/or other material. The switch portions 22 may comprise a material that is softer and/or tackier than the materials comprising the outer cylindrical portion 18, in some embodiments.

FIGS. 6A-12A and 6B-12B illustrate various attachments that may find use with the main body portion 12.

FIGS. 6A and 6B are front and perspective views, respectively, of an example embodiment of a bristle brush tool attachment 60 that may find use with a double-ended dental tool according to the present disclosure. The bristle brush tool attachment 60 may include a plurality of bristles. The bristles may be of approximately equal length, in some embodiments. In other embodiments, the bristles may be of different lengths, such that the end of the brush has a particular contour or angle. For example, the bristles may be of different lengths such that the brush angles from a proximal end to a distal end (where "proximal" refers to a portion or direction that is towards to the user's hand when the tool 10 is in use, and "distal" refers to a portion or direction that is into the user's oral cavity when the tool 10 is in use), with the distal bristles longer than the proximal bristles, for example.

FIGS. 7A and 7B are front and perspective views, respectively, of an example embodiment of an orthodontic brush tool attachment 62 that may find use with a double-ended dental tool according to the present disclosure. FIG. 14 is a top view of the example orthodontic brush tool attachment 62. The working portion 76 of the orthodontic brush tool attachment 62 may include two sets of bristles $63_1$, $63_2$, in an embodiment. The two sets of bristles $63_1$, $63_2$ may be laterally separated from each other so as to permit the two sets of bristles $63_1$, $63_2$ to clean separate portions of orthodontia simultaneously, for example. Each set of bristles $63_1$, $63_2$ may increase in length from its outer later edge to its inner lateral portion, as illustrated in FIG. 14. That is, inwardly-disposed bristles may be longer than more outwardly-disposed bristles, in some embodiments. As a result, each set of bristles $63_1$, $63_2$ may substantially form a wedge shape, with the thicker part of the wedge inward of the thinner part of the wedge. In addition, as shown in FIG. 7B, each set of bristles $63_1$, $63_2$ may increase in length from a proximal-most portion to a longitudinal midpoint, then decrease in length from the longitudinal midpoint to a distal-most portion.

FIGS. 8A and 8B are front and perspective views, respectively, of an example embodiment of a scaler tool attachment 64 that may find use with a double-ended dental tool according to the present disclosure. FIG. 15 is a cross-sectional view of the example scalar tool attachment 64. The scaler tool attachment 64 may include a scaler tip comprising a polymer material or other appropriate material. The scaler tip may include a pointed tip, in an embodiment. The scaler tip may further include a concave inner portion below the pointed tip, and two reduced-thickness outer portions below the pointed tip, in an embodiment. Accordingly, the scaler tip may gradually reduce in thickness towards the pointed tip, in an embodiment.

FIGS. 9A and 9B are front and perspective views, respectively, of an example embodiment of a scaler with mirror tool attachment 66 that may find use with a double-ended dental tool according to the present disclosure. The scaler with mirror tool attachment 66 may be substantially the same as the attachment $16_2$ illustrated in FIGS. 1 and 5. The scaler with mirror tool attachment 66 may include a mirror having a magnification of between 2.5× and 5×, in an embodiment. The scaler with mirror tool attachment 66 may further include a scaler tip comprising a polymer material or other appropriate material. The scaler tip may include a pointed tip, in an embodiment. The scaler tip may further include a concave inner portion below the pointed tip, and two reduced-thickness outer portions below the pointed tip, in an embodiment. Accordingly, the scaler tip may gradually reduce in thickness towards the pointed tip, in an embodiment.

FIGS. 10A and 10B are front and perspective views, respectively, of an example embodiment of a scraper tool attachment 68 that may find use with a double-ended dental tool according to the present disclosure. The scraper tool attachment 68 may comprise a polymer material or other appropriate material. The scraper may include a flattened, thin edge on its distal end. The flattened edge may be configured for scraping a user's teeth, in an embodiment. The scraper may include a curved portion leading to the flattened edge, in an embodiment. The scraper may gradually reduce in thickness from proximal end to distal end, in some embodiments.

FIGS. 11A and 11B are front and perspective views, respectively, of an example embodiment of a scraper with mirror tool attachment 70 that may find use with a double-ended dental tool according to the present disclosure. The scraper and mirror features of the scraper with mirror tool attachment 70 may be substantially similar to the scaper and mirror features otherwise described in this disclosure.

FIGS. 12A, 12B, and 13 are front, perspective, and perspective views, respectively, of an example embodiment of a mirror tool attachment 72 that may find use with a double-ended dental tool according to the present disclosure. The mirror feature of the mirror tool attachment 72 may be substantially similar to the mirror features otherwise described in this disclosure.

FIGS. 16A-18 illustrate portions of an example embodiment of a scraper tool attachment 84 that may find use with a double-ended dental tool 10 according to the present disclosure. The scraper tool attachment 84 may be configured to permit selective rotation of the working element—that is, the scraping tip—to enable a wide variety of uses (e.g., to access different portions of a user's oral cavity with the working tip of the scraper in a comfortable position). Except as described differently herein, the scraper tool attachment 84 may include the features of the scraper tool attachment 68.

Figure 16B:
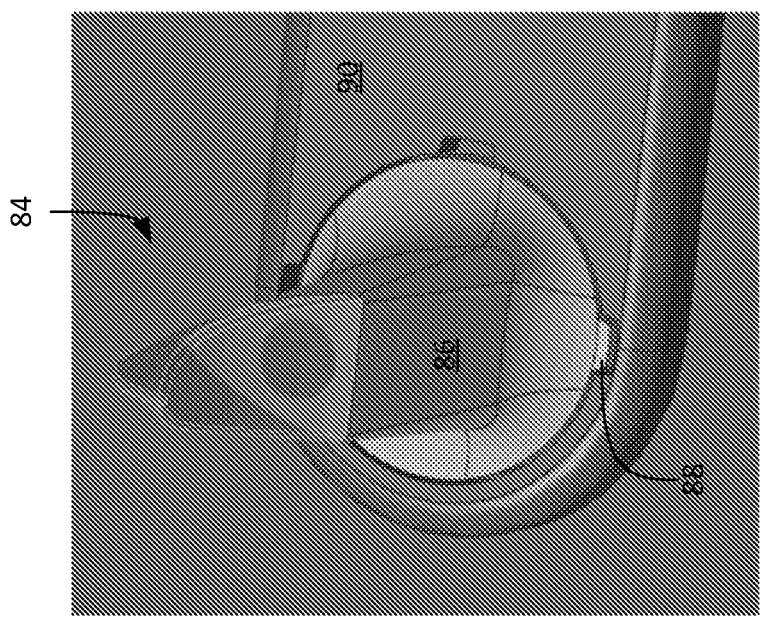
FIGS. 16A and 16B are perspective views of a portion of an example embodiment of a scraper tool attachment that may find use with a double-ended dental tool according to the present disclosure.
Figure 16A:
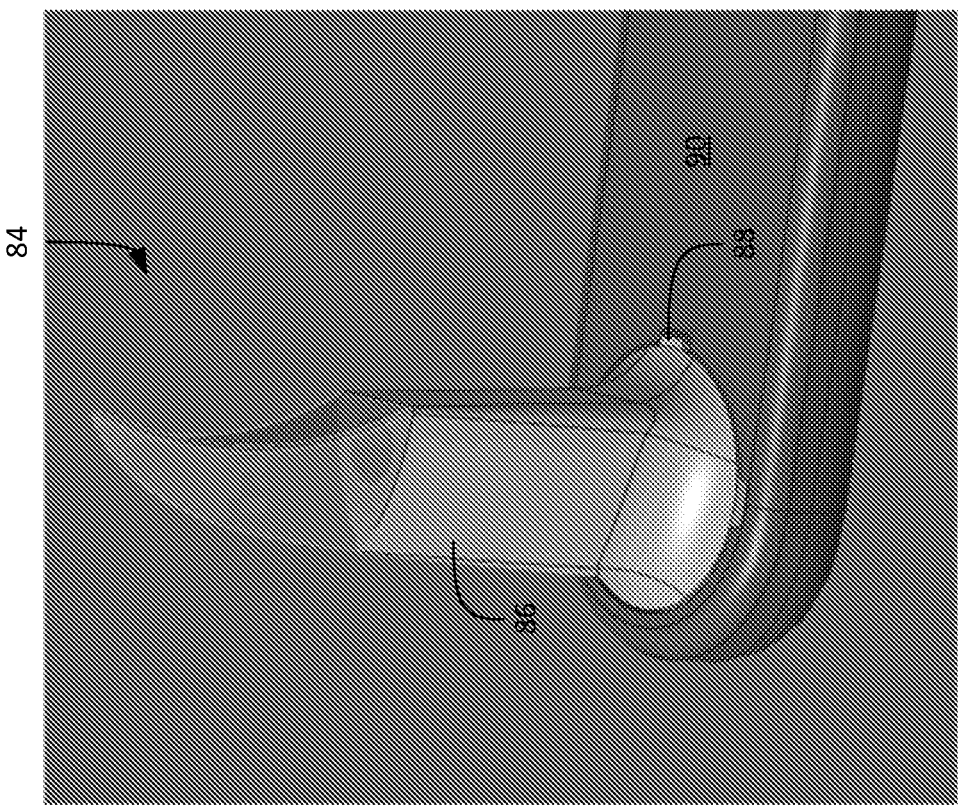
Figure 18:
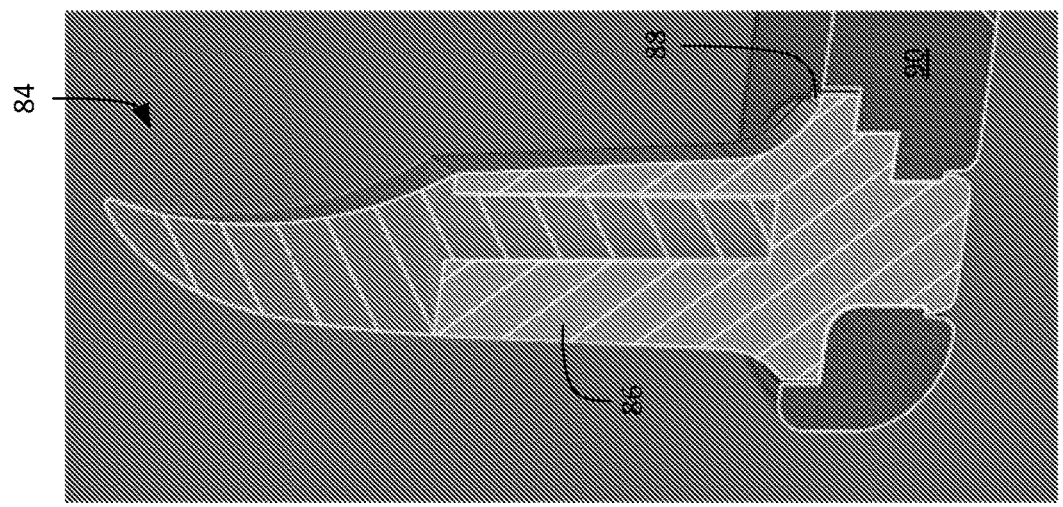
FIG. 18 is a perspective cross-sectional view of a portion of the example scraper tool attachment of FIGS. 16A and 16B.
Figure 17:
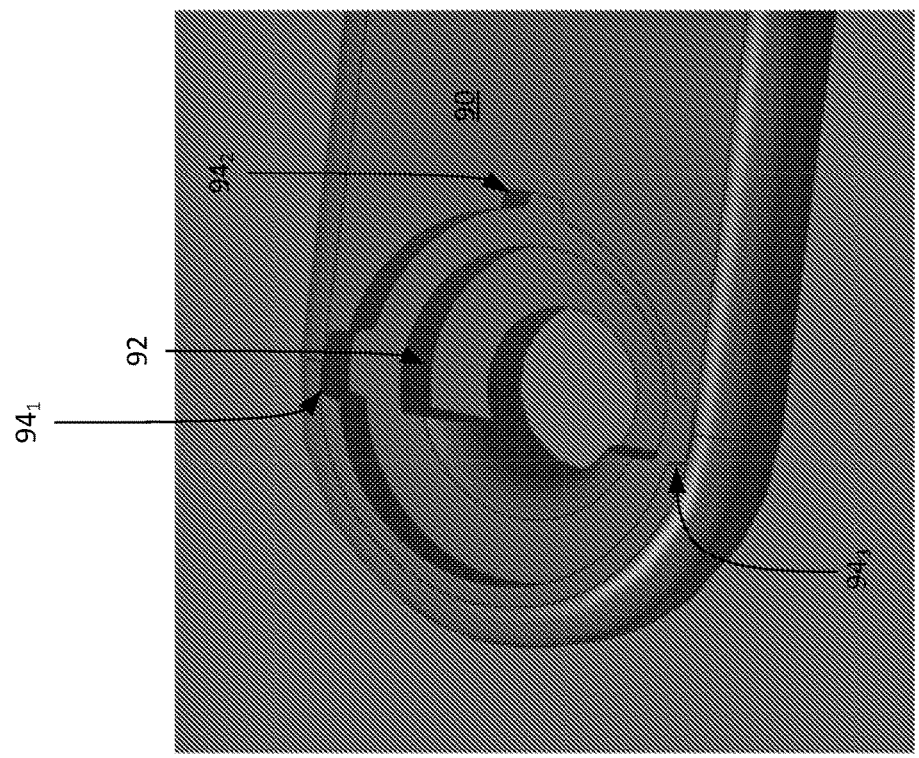
FIG. 17 is a perspective view of a portion of the example scraper tool attachment of FIGS. 16A and 16B.

The scraper tool attachment 84 may include a removable working tip 86 which includes a lateral protrusion 88. FIGS. 16A, 16B, and 18 illustrate the working tip 86; FIG. 17 omits the working tip 86 for clarity of illustration of other features. The removable working tip 86 may be insertable into (and thus mechanically coupled with) a neck 90. As shown in FIG. 17, the neck 90 may define a receiving formation 92 to receive the working tip 86. The receiving formation 92 may include one or more recesses 94 configured to receive the lateral protrusion 88 of the working tip 86. Three such recesses $94_1$, $94_2$, $94_3$ are illustrated in the embodiment of FIGS. 16A-18. The recesses may be disposed at 90-degree offsets with respect to one another, in an embodiment, as illustrated in FIG. 17. In FIGS. 16A and 18, the working tip 86 is inserted such that the lateral protrusion 88 is disposed in recess $94_2$. In FIG. 16B, the working tip 86 is inserted such that the lateral protrusion 88 is disposed in recess $94_3$. As a result, the working tip 86 is rotated 90 degrees in FIG. 16B relative to FIGS. 16A and 18.

Figure 19B:
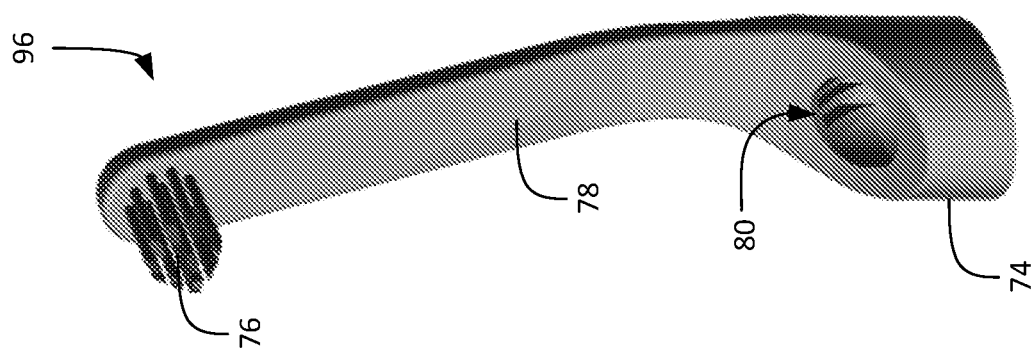
FIGS. 19A and 19B are front and perspective views, respectively, of an example embodiment of an interproximal brush tool attachment that may find use with a double-ended dental tool according to the present disclosure.
Figure 19A:
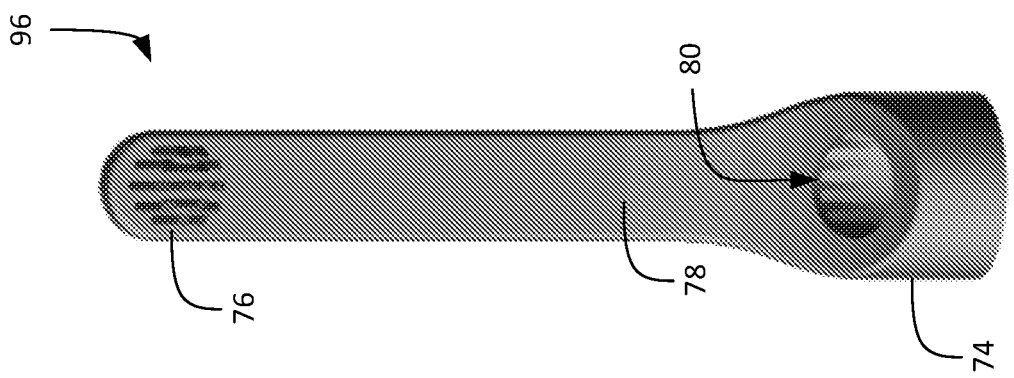

FIGS. 19A and 19B are front and perspective views, respectively, of an example embodiment of an interproximal brush tool attachment 90 that may find use with a double-ended dental tool according to the present disclosure. The interproximal brush tool attachment 90 may include a set of bristles that taper from center to edge in all lateral directions. Accordingly, the center of the bristle set includes the longest bristles, and the edges of the bristle set includes the shortest bristles. This interproximal brush tool attachment 90 may be particularly well-suited for cleaning between the user's teeth in the space where the gum and teeth meet.

Any of the attachments 60, 62, 64, 66, 68, 70, 72, 84, 90, or other appropriate attachment, may find use as an attachment $14_1$, $14_2$ with the main body portion 12. The attachments 60, 62, 64, 66, 68, 70, 72, 84, 90 may be interchangeable used on either end $14_1$, $14_2$ of the main body portion 12, in embodiments.

Each attachment 60, 62, 64, 66, 68, 70, 72, 84, 90 may include a base portion 74, a working portion 76, and a neck 78 that extends from the base portion 74 to the working portion 76. The respective working portion 76 of each attachment 60, 62, 64, 66, 68, 70, 72, 84, 90 may include one or more components for observing or treating a user's oral cavity. For example, the working portion 76 of the bristle brush tool attachment 60 comprises a plurality of soft bristles for brushing, the working portion 76 of the orthodontic brush tool attachment 62 includes two sets of stiff bristles separated and shaped so as to clean orthodontia, the working portion 76 of the scaler tool attachment 64 includes a stiff, pointed working tip for cleaning between teeth and at the interface of teeth and gums, and so on.

The base portion 74 may define a longitudinal aperture 80. As shown in FIGS. 5, 13, and 15, an inner surface of the base portion 74 may include a receiving formation 82 or other mating structure that is complementary with a mating structure on the main body portion 12, such as the protrusion 30. As shown in FIG. 5, the base portion 74—and thus the attachment 60, 62, 64, 66, 68, 70, 72, 84, 90—may be coupled to the main body portion 12 by inserting the base portion 74 over the longitudinal end of the main body portion 12 such that at least a portion of the reduced-diameter portion 28 of the main body portion 12 (e.g., the light housing 38) extends into and at least partially through the longitudinal aperture 80 of the base portion 74. The base portion 74 may be secured to the main body portion by coupling of the receiving formation 82 with the protrusion 30 (e.g., a snap-fit), as well as by friction of contact between the base portion 74 and the outer cylindrical portion 18, and between the base portion 74 and the light housing 38. As noted above, the outer cylindrical portion 18 and the light housing 38 may be spaced apart from one another so as to define an annular space, and the base portion 74 may insert into that annular space so as to be held by friction with both the outer cylindrical portion 18 and the light housing 38. When an attachment 60, 62, 64, 66, 68, 70, 72, 84, 90 is coupled with the main body portion 12, the longitudinal axis A may extend through the aperture 80.

In addition to providing a coupling means and a means by which a light source 32 may project light onto a working portion 76 of the attachments 60, 62, 64, 66, 68, 70, 72, 84, 90, the aperture 80 may additionally serve as a safety precaution. Although the attachments 60, 62, 64, 66, 68, 70, 72, 84, 90 include robust features for ensuring a secure connection between the attachments 60, 62, 64, 66, 68, 70, 72, 84, 90 and the main body portion, in the unlikely event that an attachment 60, 62, 64, 66, 68, 70, 72, 84, 90 becomes inadvertently dislodged from the main body portion 12 and is partially swallowed by a user, the aperture 80 will allow the passage of air so as to prevent choking by the user.

When an attachment 60, 62, 64, 66, 68, 70, 72, 84, 90 is coupled with the main body portion 12, the attachment 60, 62, 64, 66, 68, 70, 72, 84, 90 may be substantially radially flush with the main body portion 12, in some embodiments. That is, an outer diameter of the base portion 74 may be substantially the same as an outer diameter of the main body portion that is immediately longitudinally adjacent to the base portion 74, such that the base portion 74 of the attachment 60, 62, 64, 66, 68, 70, 72, 84, 90 may maintain the outer profile of the main body portion 12, as illustrated in FIGS. 1 and 5.

When an attachment 60, 62, 64, 66, 68, 70, 72, 84, 90 is coupled with the main body portion 12, the distal surface of the base portion 74 may be substantially flush with the light-transmissive cover 40, in some embodiments. That is, the base portion 74 and the light-transmissive cover 40 may appear to collectively define a substantially flat surface, as illustrated in FIGS. 1 and 5.

The base portion 74, neck portion 78, and one or more portions of the working portion 76 may comprise a monolithic body of material, in embodiments. That material may be, for example, a polypropylene material or other polymer.

The tool 10 and attachments 60, 62, 64, 66, 68, 70, 72, 84, 90 may provide many functional advantages. First, each of the attachments 60, 62, 64, 66, 68, 70, 72, 84, 90 may effectively clean a user's teeth, a portion thereof, or an orthodontic treatment, and/or allow the user to view the user's oral cavity. Second, the attachments 60, 62, 64, 66, 68, 70, 72, 84, 90 may be selectively couplable with the main body portion 12, thus allowing a user to customize a personal tool 10 and to use many different attachments with a single main body portion 12. Third, a wide variety of attachments may be available, in embodiments, further enhancing the customizability of the tool 10. Fourth, the tools that may be available for the scaler 10 may be sufficiently durable that a user can use each tool numerous times before the tool requires replacement. Fifth, the ends of the main body portion may be curved in opposite directions, such that the tools extends in opposite directions from the main body portion, thereby enabling the user to quickly and easily flip the scaler in his or her hand to use the opposite end of the scaler 10 (e.g., the tool on the opposite end).

It should be noted that various changes and modifications to the present embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

While this disclosure has described certain embodiments, it will be understood that the claims are not intended to be limited to these embodiments except as explicitly recited in the claims. On the contrary, the instant disclosure is intended to cover alternatives, modifications and equivalents, which may be included within the spirit and scope of the disclosure. Furthermore, in the detailed description of the present disclosure, numerous specific details are set forth in order to provide a thorough understanding of the disclosed embodiments. However, it will be obvious to one of ordinary skill in the art that systems and methods consistent with this disclosure may be practiced without these specific details. In other instances, well known methods, procedures, components, and circuits have not been described in detail as not to unnecessarily obscure various aspects of the present disclosure.

What is claimed is:

1. A dental tool comprising:
    a main body portion having a first longitudinal end and a second longitudinal end, wherein the first end and the second end define respective reduced diameter portions;
    two or more tool attachments, each tool attachment comprising a working portion and a base portion, the base portion configured to be removably coupled to either of the reduced-diameter portions of the main body portion so as to secure the tool attachment to the main body portion; and
    a light source, disposed within the main body portion, arranged so as to illuminate the working portion of one of the tool attachments when the one of the tool attachments is coupled to the first end of the main body portion and the light source is electrically coupled to a power source;
    wherein:
        the respective base portion of each of the two or more tool attachments defines an aperture; and
        a portion of the main body portion extends through the aperture of any one of the tool attachments when the one of the tool attachments is coupled to the main body portion.

2. The dental tool of claim 1, wherein:
    the main body portion defines a longitudinal axis; and
    the longitudinal axis extends through the aperture of any one of the tool attachments when the one of the tool attachments is coupled to the main body portion.

3. The dental tool of claim 1, wherein the light source projects light from the reduced-diameter portion of the first end.

4. The dental tool of claim 1, wherein an outer diameter of the base portion of any one of the tool attachments is substantially the same as an outer diameter of the main body portion that is immediately longitudinally adjacent to the base portion when the one of the tool attachments is coupled to the main body portion.

5. The dental tool of claim 1, further comprising:
    a battery disposed within the main body portion; and
    a switch disposed on or in the main body portion, the switch configured to selectively couple the light source to the battery responsive to user actuation of the switch.

6. The dental tool of claim 1, wherein the main body portion is substantially cylindrical along its entire longitudinal length.

7. The dental tool of claim 1, wherein the light source is a first light source, further comprising:
- a second light source, disposed within the main body portion, arranged so as to illuminate the working portion of one of the tool attachments when the one of the tool attachments is coupled to the second end of the main body portion and the second light source is electrically coupled to a power source.

8. The dental tool of claim 7, wherein:
- the first light source projects light at a first angle relative to a longitudinal axis of the main body portion;
- the second light source projects light at a second angle relative to the longitudinal axis; and
- the first angle has substantially the same absolute value as the second angle.

9. The dental tool of claim 7, wherein the first light source is arranged to project light in a first direction, the second light source is arranged to project light in a second direction, and the first direction is radially opposite the second direction.

10. The dental tool of claim 7, further comprising:
- a battery disposed within the main body portion;
- a first switch disposed on or in the main body portion, the switch configured to selectively couple the first light source to the battery responsive to user actuation of the first switch; and
- a second switch disposed on or in the main body portion, the second switch configured to selectively couple the second light source to the battery responsive to user actuation of the second switch;
- wherein the second switch is radially opposite the first switch.

11. The dental tool of claim 1, wherein the two or more tool attachments comprise two or more of:
- a bristle brush tool attachment;
- an orthodontic brush tool attachment;
- a scaler tool attachment;
- a scaler with mirror tool attachment;
- a scraper tool attachment;
- a scraper with mirror tool attachment;
- a mirror tool attachment; or
- an interproximal brush tool attachment.

12. The dental tool of claim 1, wherein the two or more tool attachments comprise an orthodontic brush tool attachment comprising two sets of bristles that are laterally separated from each other, wherein bristles within each set increase in length from an outer later edge of the orthodontic brush tool attachment to an inner lateral portion of the orthodontic brush tool attachment.

13. A dental tool comprising:
- a main body portion having a first longitudinal end and a second longitudinal end, wherein the first end and the second end define respective reduced diameter portions;
- two or more tool attachments, each tool attachment comprising a working portion and a base portion, the base portion configured to be removably coupled to either of the reduced-diameter portions of the main body portion so as to secure the tool attachment to the main body portion; and
- a light source, disposed within the main body portion, arranged so as to illuminate the working portion of one of the tool attachments when the one of the tool attachments is coupled to the first end of the main body portion and the light source is electrically coupled to a power source; and
- a light-transmissive cover disposed at the reduced-diameter portion of the first end, wherein the light source and the light-transmissive cover are arranged such that the light source emits light through the light-transmissive cover;
- wherein the light-transmissive cover is flush with a surface of the base portion of any one of the tool attachments when the one of the tool attachments is coupled to the main body portion;
- wherein the light source projects light from the reduced-diameter portion of the first end.

14. A dental tool comprising:
- a main body portion having a first longitudinal end and a second longitudinal end, wherein the first end and the second end define respective reduced diameter portions;
- two or more tool attachments, each tool attachment comprising a working portion and a base portion, the base portion configured to be removably coupled to either of the reduced-diameter portions of the main body portion so as to secure the tool attachment to the main body portion; and
- a light source, disposed within the main body portion, arranged so as to illuminate the working portion of one of the tool attachments when the one of the tool attachments is coupled to the first end of the main body portion and the light source is electrically coupled to a power source;
- wherein the two or more tool attachments comprise a scaler tool attachment, the scaler tool attachment comprising a removable working tip that is insertable into a receiving formation of a neck of the scaler tool attachment, the removable working tip comprising a lateral protrusion, wherein the receiving formation defines two or more recesses configured to receive the lateral protrusion of the working tip, whereby the removable working tip may be coupled in two or more positions relative to the neck.

* * * * *